US00PP15723P3

(12) United States Plant Patent
Eremin

(10) Patent No.: US PP15,723 P3
(45) Date of Patent: Apr. 19, 2005

(54) *PRUNUS* PLANT NAMED 'VSL-2'

(50) Latin Name: *Prunus fruticosa×p. lannesiana*
Varietal Denomination: VSL-2

(75) Inventor: Guennadi Eremin, Krymsk (RU)

(73) Assignee: Krymsk Breeding Station (RU)

( * ) Notice: Subject to any disclaimer, the term of this patent is extended or adjusted under 35 U.S.C. 154(b) by 202 days.

(21) Appl. No.: 09/880,953

(22) Filed: Jan. 11, 2002

(65) Prior Publication Data

US 2003/0217400 P1 Nov. 20, 2003

(30) Foreign Application Priority Data

Apr. 23, 2001 (QZ) ..... PBR 20019999

(51) Int. Cl.[7] ..... A01H 5/00
(52) U.S. Cl. ..... Plt./183
(58) Field of Search ..... Plt./183

(56) References Cited

U.S. PATENT DOCUMENTS

| | | | | | |
|---|---|---|---|---|---|
| PP4,059 | P | * | 6/1977 | Tydeman et al. | Plt./183 |
| PP5,159 | P | * | 12/1983 | Tydeman et al. | Plt./183 |
| PP5,801 | P | * | 11/1986 | Monin et al. | Plt./183 |
| PP5,802 | P | * | 11/1986 | Monin et al. | Plt./183 |
| PP5,803 | P | * | 11/1986 | Monin et al. | Plt./183 |
| PP7,924 | P | * | 7/1992 | Okada et al. | Plt./183 |
| PP8,132 | P | * | 2/1993 | Brooks et al. | Plt./183 |
| PP8,194 | P | * | 4/1993 | Brooks et al. | Plt./183 |
| PP8,852 | P | * | 8/1994 | Gruppe et al. | Plt./183 |
| PP8,954 | P | * | 10/1994 | Gruppe et al. | Plt./183 |
| PP9,622 | P | * | 8/1996 | Gruppe et al. | Plt./183 |
| PP9,623 | P | * | 8/1996 | Gruppe et al. | Plt./183 |
| PP9,630 | P | * | 8/1996 | Gruppe et al. | Plt./183 |
| PP9,631 | P | * | 8/1996 | Gruppe et al. | Plt./183 |
| PP11,233 | P | * | 2/2000 | Jacob | Plt./183 |
| PP14,126 | P3 | * | 9/2003 | Zaiger et al. | Plt./183 |
| 2002/0138884 | P1 | * | 9/2002 | Zaiger et al. | Plt./180 |
| 2003/0126654 | P1 | * | 7/2003 | Southwick | Plt./183 |
| 2003/0126655 | P1 | * | 7/2003 | Southwick | Plt./183 |

OTHER PUBLICATIONS http://www.hrt.msu.edu/faculty/Langg/Sweet_Cherry_Rootstocks.html.*
http://www.raintreenursery.com/catalog/ProductDetails.cfm?ProductD=R117.*
http://www.meadow–lake.com/shop/dept.asp?dept_id=2.*
http://www.meadow–lake.com/shop/product.asp?dept%5Fid=2&pf%Fid=2PRKR5.*
http://www.fruitcaas.net.cn/taolunyuandi/t03.htm.*
http://www.meadow–lake.com/shop/product.asp?dept_id=F&pf_id=FBIPRK5.*
Intensive orchards of stone fruits on VVA–1 rootstock. Provorchenko, A. V.; Eremin, V. G. Opytno–selektsionnaya Stantsiya VIR, 353330 Krymsk, Krasnodarski krai, Russia. Sadovodstvo i Vinogradarstvo (No. 2): p. 4–5 Publication Year: 1996.*
Eremin, G. et al. "New dwarf clone rootstocks for sweet cherry and sour cherry trees" Proceedings of the Internation Conference Fruit Production and Fruit Breeding Tatru, Estonica Sep. 12–13, 2000 p. 125–127.*

* cited by examiner

*Primary Examiner*—Bruce R. Campell
*Assistant Examiner*—W C Haas
(74) *Attorney, Agent, or Firm*—Webb Ziesenheim Logsdon Orkin & Hanson, P.C.

(57) ABSTRACT

A new and distinct rootstock variety of *Prunus* named 'VSL-2' that is characterized by an absence of suckers, a vigorous growth habit, pink flowers, the ability to serve well as rootstock that is compatible with all other cherries, and the ability to propagate well by softwood cuttings, stool beds and meristem cuttings in vitro. In combination these traits set the new cultivar apart from all other existing varieties of *Prunus* rootstock.

1 Drawing Sheet

Botanical classification: *Prunus fruticosa×p. lannesiana*. Varietal denomination: 'VSL-2'.

CROSS-REFERENCES TO RELATED APPLICATIONS

The application for the new invention *Prunus* Plant Named 'VSL-2' is co-pending with three other plant patent applications entitled *Prunus* Plant Named 'VVA-1', Ser. No. 09/880,952; *Prunus* Plant Named 'LC-52', Ser. No. 09/880,950; and *Prunus* Plant Named 'VSV-1' Ser. No. 09/880,951, having the same filing date and inventor.

BACKGROUND OF THE INVENTION

The present invention relates to the new and distinct cultivar known botanically as a hybrid of *Prunus* and referred to hereinafter as 'VSL-2'. The new invention was bred by the inventor at the Breeding Station in Krymsk, Russia.

The breeding program at the Breeding Station was established in 1976 and funded by the government of the former Soviet Union for the purpose of producing new and improved *prunus* cultivars that propagate well by methods of softwood cuttings, meristem cuttings in vitro, as well as by stool beds, and that serve well as rootstock that is compatible with other cherries.

In 1976 the inventor crossed the female *Prunus fruticosa* (not patented) with the male *Prunus lannesiana* (not patented) producing an induced hybridization in a cultivated area of Krymsk, Russia. The resulting seedlings were observed and evaluated for ten years. In 1986 the inventor selected 'VSL-2' from these seedlings. The new cultivar originated as a single plant and is a hybrid cross between *Prunus fruticosa* (not patented) and *Prunus lannesiana* (not patented).

The closest comparison plants are the parent plants. 'VSL-2' is distinguishable from the female parent *Prunus fruticosa* by larger leaves, greater vigor, pink flowers, sour fruit, and absence of suckers. 'VSL-2' is distinguishable from the male parent *Prunus lannesiana* by the absence of stipules, smaller size, dark red fruit, and the ease of propagation. The distinguishing traits that make 'VSL-2' unique from all other existing varieties of *Prunus* rootstock known to the inventor are ease of propagation, absence of suckers and the ability to serve as rootstock that is compatible with all cherries known to the inventor.

'VSL-2' was first asexually propagated in 1986 by the inventor at the Breeding Station in Krymsk, Russia. The method used was softwood cuttings. The distinguishing traits have been determined stable and are reproduced true to type in successive generations.

BRIEF DESCRIPTION OF THE DRAWING

The photograph is an illustration of the new variety, VSL-2.

SUMMARY OF THE INVENTION

The following traits have been repeatedly observed and represent the distinguishing characteristics of the new cultivar. These traits in combination distinguish 'VSL-2' from all other existing varieties of *Prunus* rootstock. 'VSL-2' has not been tested under all possible conditions and phenotypic differences may be observed with variations in environmental, climatic, and cultural conditions, however, without any variance in genotype.

1. 'VSL-2' serves as rootstock that is compatible with all other cherries.
2. 'VSL-2' propagates well by softwood cuttings, stool beds, and in vitro.
3. 'VSL-2' does not produce suckers.
4. 'VSL-2' exhibits a dwarf form.
5. 'VSL-2' is vigorous.
6. 'VSL-2' differs from the female parent *Prunus fruticosa* by increased vigor, large leaves, pink flowers, sour fruit, and absence of suckers.
7. 'VSL-2' differs from the male parent *Prunus lannesiana* by its smaller size, dark red, sour fruit, ease of propagation, and absence of stipules.

BOTANICAL DESCRIPTION OF THE PLANT

The following is a detailed botanical description of the new rootstock variety *Prunus* 'VSL-2'. Observations, measurements, values, and comparisons were collected in McMinnville, Oreg. from the inventor. The new variety was five (5) years old when described and was cultivated in a hot and moderately humid environment. The foliage, flower and fruit exhibited by this cultivar are of no economic or commercial value, therefore comparisons and botanical descriptions of the foliage, fruit and flower are made for identification purposes only. Mature specimens, as well as bareroot specimens, were unavailable for photographing at the time this document was written. The color determinations are in accordance with The R.H.S. Colour Chart of the Royal Horticultural Society, London, England except where general color terms of ordinary dictionary significance are used.

Botanical classification: *Prunus* 'VSL-2'.
Parentage: *Prunus* 'VSL-2' is an induced hybrid that resulted from crossing the following plants.
*Female parent.*—*Prunus fruticosa* (not patented).
*Male parent.*—*Prunus lannesiana* (not patented).
Type: Deciduous tree.
Use: 'VSL-2' serves well as rootstock for all other cherries known to the inventor.
Soil: All soils.
Light: Full sunlight.
Fruit bearing: None.
Crop time: Requires 3 years from a rooted cutting to achieve finished product size ready to ship bareroot (1 year rootstock and 2 years with scion variety).
Dimensions at crop time: 2.5 m in height and 2 m. in width.
Vigor: 50–60% of standard using *Prunus avium* as standard (sweet cherry seedling).
Habit: Dwarf and erect.
Hardiness: USDA Zone 5A.
Cold tolerance: Excellent.
Heat tolerance: Excellent.
Disease resistance: No diseases observed; high resistance to mildew.
Propagation: Propagation can be accomplished by softwood cuttings, stool beds and meristem cuttings in vitro.
rooting habit: Fine and fibrous initially. After 1 year, roots become fleshy and thick.
Time to initiate roots: 6 months is required to develop roots at 22–25° Centigrade.
Disease and insect resistance: Normal resistance to disease and insects.
Trunk:
*Trunk dimensions* (*at 3 years*).—5 cm. in diameter and 20 cm. in height above soil.
*Trunk bark surface.*—Glabrous surface.
*Trunk bark color.*—178B.
*Lenticels.*—Present.
*Lenticel dimensions.*—2–3 mm. in length and 1 mm. in width.
*Lenticel shape.*—Lens shaped.
*Lenticel color.*—198B.
Branches:
*Branch surface.*—Glabrous surface.
*Branch color.*—175B.
*Internode length.*—5–10 cm. between nodes.
*Branching angle at emergence.*—70° angle.
*Branching habit.*—Freely branching.
*Branch pubescence.*—Absent.
*Branch lenticels.*—Present.
*Lenticels.*—Present on all branches.
*Lenticel shape.*—Lens shaped.
*Lenticel color.*—198B.
*Lenticel dimensions.*—2–3 mm. in length and 1 mm. in width.
*Lenticel number.*—9 per inch on 2-year old rootstocks.
Leaves:
*Arrangement.*—Alternate and whorled.
*Leaf length.*—4–4.5 cm. in length.
*Leaf width.*—3–3.5 cm. in width.
*Leaf shape.*—Lanceolate.
*Leaf apex.*—Acuminate.
*Leaf base.*—Rounded.
*Leaf color* (*adaxial surface*).—135D.

*Leaf color* (*abaxial surface*.—136B.
*Leaf surface* (*adaxial*).—Glabrous surface.
*Leaf surface* (*abaxial*).—Glabrous surface.
*Leaf margins*.—Crenulate. Young leaves involuted.
*Leaf division*.—Simple.
*Petiole dimensions*.—1.2 cm. in length and 1 mm. in width.
*Petiole color*.—140C.
*Petiole surface*.—Glabrous.
*Stipules*.—Absent.
*Leaf pubescence*.—Absent.
*Venation pattern*.—Pinnate with prominent mid-vein.
*Vein color* (*adaxial and abaxial surfaces*).—135D.
*Leaf texture*.—Smooth texture.
*Leaf strength*.—Moderate strength.
*Leaf appearance*.—Glossy with young leaves involuted.

Fruit:
*Maturity*.—Requires 60–65 days to mature.
*Dates of picking*.—Not a fruit crop. Fruit has no commercial value.
*Production*.—Minimal.
*Fruit form*.—Globose.
*Stem dimensions*.—2–2.5 cm. in length and 1 mm. in width.
*Stem color*.—144A.
*Skin color*.—53A.
*Skin surface*.—Glabrous surface.
*Lenticels*.—Absent.
*Flesh color*.—53A.
*Flesh texture*.—Juicy.
*Flavor*.—Bitter.
*Aroma*.—None.
*Seed number*.—One drupe.
*See shape*.—Round.
*Seed color*.—164A.
*Seed dimensions*.—5–6 mm. in diameter and 5–6 mm. in length.
*Keeping quality*.—None.
*Storage*.—Not determined because the fruit has no commercial value.
*Use*.—Fruit is not recommended for consumption and has no commercial value.

Flower:
*Arrangement*.—Solitary.
*Flower shape*.—Rotate.
*Bud dimensions*.—3 mm. in width and 3 mm. in length.
*Bud color*.—56C.
*Time of bloom*.—Flowers bloom at when plant is 1 year and flowers last for 7–8 days.
*Flower diameter*.—2.5–3 cm. in diameter.
*Flower depth* (*throat*).—2–2.5 mm. in depth.
*Bloom quantity*.—40–50 flowers per branch.
*Number of petals*.—Five petals in number.
*Fused or unfused*.—Petals are unfused.
*Petal shape*.—Oval.
*Petal margin*.—Entire and wavy.
*Flower color fully opened* (*upper and lower surfaces*).—56D.
*Dimensions of peduncle*.—2 cm. in length and 1 mm. in width.
*Color of peduncle*.—144A.
*Surface of peduncle*.—Glabrous surface.
*Calyx dimensions*.—2–3 mm. in length and 7–8 mm. in width.
*Calyx surface*.—Glabrous surface.
*Pubescence*.—Absent.
*Calyx color*.—152A.
*Number of sepals*.—Five sepals in number.
*Natural flowering season*.—Spring.
*Persistent or self-cleaning*.—Self-cleaning.
*Fragrance*.—None.

Reproductive organs:
*Stamen number*.—Polyandrous. 20–25 stamens and unequal lengths.
*Stamen color*.—145C.
*Anther shape*.—Round with stamen attached at center of dorsal surface.
*Anther color*.—9B.
*Anther dimensions*.—1 mm. in length and 1 mm. in width.
*Amount of pollen*.—Heavy amount.
*Color of pollen*.—9B.
*Pistil*.—One in number.
*Pistil color*.—144C.
*Pistil dimensions*.—1 cm. in length and 0.50 mm. in width.
*Style color*.—144C.
*Style shape*.—Elongate.
*Style dimensions*.—1 mm. in length and 0.50 mm. width.
*Ovary dimensions*.—2 mm. in length and 2 mm. in width.
*Ovary color*.—144B.
*Ovary position*.—Superior.

I claim:

1. A new and distinct variety of *Prunus* plant named 'VSL-2', as herein described and illustrated.

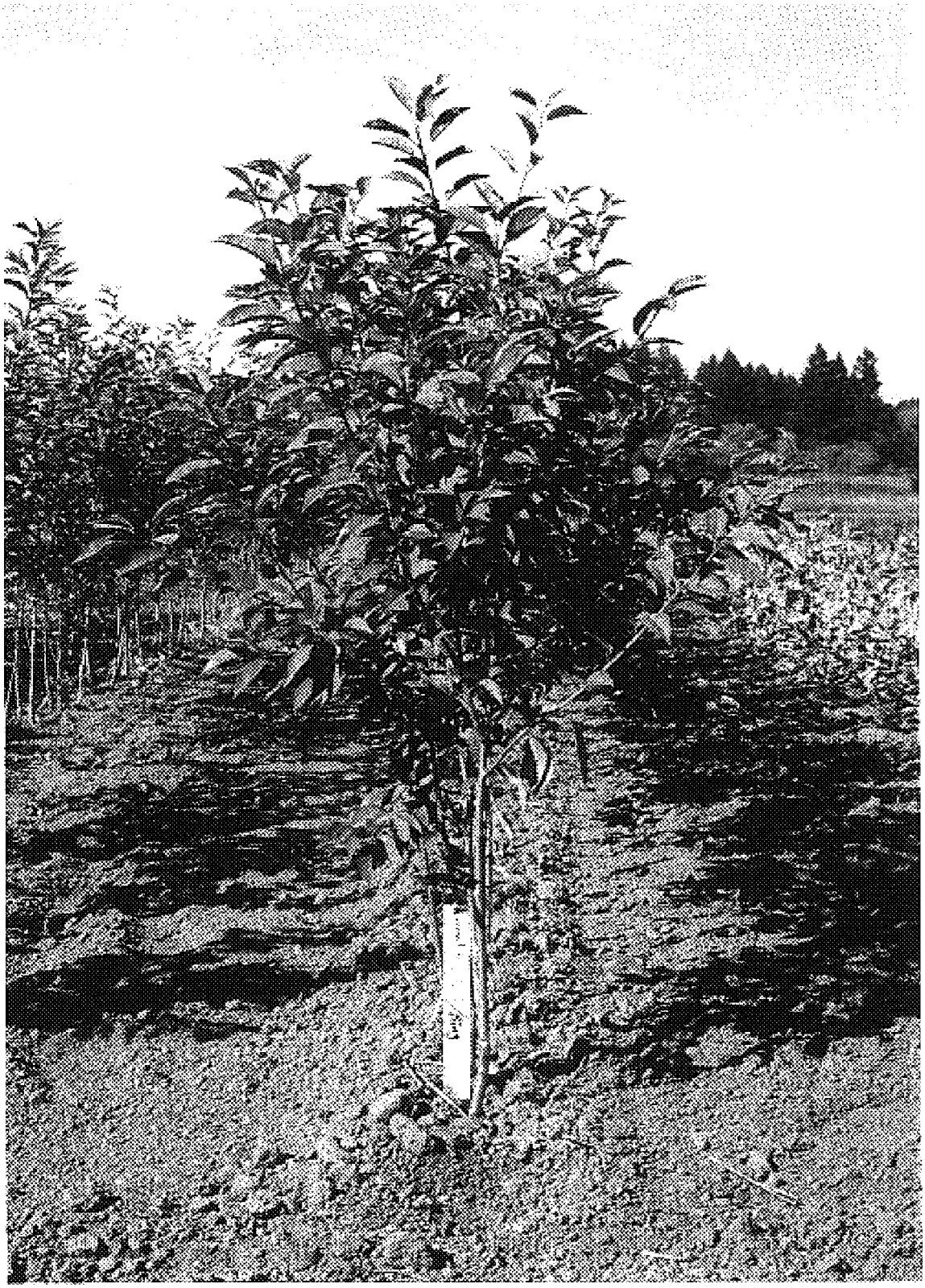

* * * * *